United States Patent [19]

Brandely et al.

[11] Patent Number: 5,219,565
[45] Date of Patent: Jun. 15, 1993

[54] TREATMENT OF PRIMARY CANCERS OF THE PLEURA

[75] Inventors: Maud Brandely; Danielle Lando, both of Paris, France

[73] Assignee: Roussel Uclaf, France

[21] Appl. No.: 535,775

[22] Filed: Jun. 8, 1990

[30] Foreign Application Priority Data

Apr. 17, 1990 [FR] France .................. 90 04895

[51] Int. Cl.⁵ .................. A61K 45/05; A61K 37/02
[52] U.S. Cl. .................. 424/85.2
[58] Field of Search .................. 424/85.2

[56] References Cited

FOREIGN PATENT DOCUMENTS 31539 10/1983 European Pat. Off. .
353150 1/1990 European Pat. Off. .

OTHER PUBLICATIONS

Stedman's Medical Dictionary 24th edition (1982) pp. 216, 707-708, 829 & 1100.
Yasumoto et al. Cancer Research 47, Apr. 19, 1987 pp. 2184-2187.
Kato et al. Biochem. & Biophys. Research Comm. vol. 130, No. 2, 1985 pp. 692-699.
Thatcher et al. Cancer Treatment Reviews vol. 16, SupA. pp. 161-162, 1989.
Flechter, et al., Lymphokine Research, vol. 6 (1987) pp. 45 to 57.
Rosenberg, et al, N. Eng. J. Med., vol. 316 (1987) pp. 889 to 897.
Antman, N. Eng. J. Med., vol. 303 (1980) pp. 200 to 202.
Antman, Am. J. Med., vol. 68 (1980) pp. 356 to 362.
Manning et al., Am. Rev. Respir. Dis., (Abstract only).
Bradley et al, 3rd Int. Conference on Malignant Lymphona Jun. 19, 1987 p. 87.
Taniguchi et al., Nature, vol. 302 (1983) pp. 305 to 306.
Ju et al., J. Biol. Chem (1987), vol. 262 pp. 5723 to 5731.
Mossman et al., Immunol. Meth (1983), vol. 65, pp. 55 to 63.

Primary Examiner—Christine M. Nucker
Assistant Examiner—Choon Koh
Attorney, Agent, or Firm—Bierman & Muserlian

[57] ABSTRACT

A method for treating primary cancers of the pleura in humans comprising administering to humans an amount of a polyprotein having human interleukin activity sufficient to treat primary cancers of the pleura.

15 Claims, No Drawings

TREATMENT OF PRIMARY CANCERS OF THE PLEURA

STATE OF THE ART

IL2 which is a lymphokine produced by the activated T lymphocytes, possesses an immuno-modulatory activity and an antitumor activity described for example by Fletcher et al. (Lymphokine Research, Vol. 6 (1987), p. 47 to 57) which activities include in particular the ability to initiate the proliferation of T lymphocytes and the induction of cyto-toxicity of the NK cells (natural killer) and the LAK cells (lymphokine activited killer). It has been observed that the administration of IL2 either on its own at a high dose or combined with LAK cells can induce the regression of certain cancers established in mice and in patients having metastatic cancers such as melanoma, cancer of the kidney, colorectal cancer or non-Hodgkin's lymphoma (Rosenberg, et al., N. Eng. J. Med., 1987, Vol. 316, p. 889 to 897).

Primary cancers of the pleura include essentially diffuse mesotheliomas and less commonly sarcomas for which existing treatments of surgery, chemotherapy or radio-therapy on their own or in combination with each other do not show a recognized effectiveness. Thus malignant mesothelioma, whose association with exposure to asbestos was suggested, then confirmed (Antman Eng. J. Med., 1980, Vol. 303, p. 200 to 202) in 10 to 70% of cases (Antman et al., Am. J. Med., 1980, Vol. 68, p. 356 to 362) and localized in the pleura more frequently than in the peritoneum (ratio about 2.5/1), develops fatally over a few months, in the absence of effective treatment.

It has been shown in vitro on cell lines or on fresh cells of human malignant mesothelioma that the mesothelioma cells are resistant (>99.9%) to lysis by NK cells, but relatively sensitive (58%) to lysis by LAK cells (Manning et al., Am. Rev. Respir. Dis., June, 1989, Vol. 139, p. 1369 to 1374).

Clinical studies were carried out, in particular with an analog of IL2 combined with an adoptive immuno-therapy for patients with various tumors. An objective anti-tumor activity was only reported for cancer of the kidney, melanoma, cancer of the colon and lymphoma. Mesothelioma is quoted in the list of tumors studied which might have shown a regression (Bradley et al., Third International Conference on Malignant Lymphoma., June 10 to 13, Lugano 1987, p. 26).

None of the clinical results showed the effectivness of the therapy for primary cancers of the pleura with IL2 on its own, notably in 3 patients suffering from mesothelioma, having received an administration by intravenous route (Thatcher et al., Cancer Treatment Reviews, Vol. 16, Suppl. A., p. 161 to 162. June, 1989).

OBJECTS OF THE INVENTION

It is an object of the invention to provide a novel method of treating primary cancers of the pleura in humans.

This and other objects and advantages of the invention will become obvious from the following detailed description.

THE INVENTION

The novel method of the invention for the treatment of primary cancers of the pleura in humans comprises administering to humans an amount of polypeptide having human interleukin activity sufficient to treat primary cancers of the pleura.

By polypeptide having the activity of human IL2 is meant natural human IL2, recombinant human IL2, that is, obtained by the technology of recombinant DNA, for example as described by Taniguchi, T. et al., (Nature, (1983, Vol. 302, p. 305 to 310) or in the Patent EP 9,1530 B, alleles or derivatives of these products as described for example by Ju et al., (J. Biol. Chem., (1987), Vol. 262, p. 5723 to 5731).

The primary cancers of the pleura that the invention relates to include cancers such as pleural mesothelioma and sarcoma, generally clinically characterized by a pleural effusion, especially when the cancer of the pleura is a mesothelioma.

Pleural mesothelioma is generally clinically characterized by chest pains or respiratory difficulties combined with a pleural effusion and its diagnosis differentiates it from inflammatory pleurisy, primary lung cancer or metastases resulting from another primary cancer. The invention describes the use of human IL2 in a treatment whose effectiveness is shown by a response rate of about 50% in patients suffering from pleural mesothelioma, optionally having undergone a surgical excision but no previous chemotherapy or radiotherapy treatment. Especially useful as the polypeptide having the activity of human IL2 is a pure recombinant IL2.

The pharmaceutical compositions prepared according to the invention contain a recombinant human IL2, alleles or derivatives of the latter, as described above, for which purification techniques known to the expert are used, which allow the preparation of pure products.

A more particular subject of the invention is the use as the IL2 of a non-glycosylated recombinant IL2 in reduced form. The non-glycosylated IL2 used is that having the sequence of natural IL2 with 133 amino-acids, optionally with an additional N-terminal methionine, of which the 3 cysteines in position 58, 105 and 125 are in reduced form and demonstrates a biological activity comparable to that of oxidized IL2 having the same sequence including a disulfide bridge in position 58-105. The reduced IL2 is described in European Patent Application EP 0,353,150. By reduced form is meant that the cysteine residues contained by the IL2 include a free sulfhydryl group, the determination of which is carried out, for example, by spectrophotometry with dithiodipyridine as reagent for the thiols.

The biological activity is determined by measuring the proliferation of the leucemic cell lines of mice dependent on IL2, CTLL-2, with a colormetric test using tetrazolium salt (Mossman et al, Immunol. Meth., (1983), Vol. 65, p. 55 to 63). The specific activity of the recombinant IL2 used in the invention is at least equal to $0.5 \times 10^6$ U BRMP/mg, preferably at least equal to $1 \times 10^7$ U BRMP/mg. The unit of IL2 activity is defined as the quantity which produces 50% of the maximum response in the test. A sample provided by the National Cancer Institute (NCI), "Biological Response Modifier Programm (BRMP) reference agent human IL2 (jurkat)", is used as a standard.

Preferably, the IL2 is administered intrapleurally at a dose of 2 to $25 \times 10^6$ U/M² by injection, and more especially the IL2 is administered at a dose of $15 \times 10^6$ U/M² per day. More preferably, the IL2 is administered in cycles of 5 consecutive days and is characterized in that the IL2 is administered repeatedly for at least 2 non-consecutive cycles. The dose administered, the frequency of the injection and the duration of the treatment vary as a function of the patent's condition.

The IL2 is contained in a pharmaceutical composition, preferably lyophilized in a dosage-flask containing 0.1 to 2 mg of active ingredient and is reconstituted with distilled water for injection. The solution obtained is immediately diluted with a solute, for example 5% glucose, for administration by intrapleural perfusion. In a preferred method, the IL2 is the above-mentioned reduced recombinant IL2, an example of the pharmaceutical preparation of which is given hereafter, the dose is $15 \times 10^6$ U/M$^2$ per day, following a cycle of 5 consecutive days repeated twice, spaced out over a period of about 5 weeks, representing about $225 \times 10^6$ U/M$^2$ and about 21 mg of IL2 administered in total to the patient, by continuous perfusion by intrapleural route.

In the following examples, there are described several preferred embodiments to illustrate the invention. However, it should be understood that the invention is not intended to be limited to the specific embodiments.

EXAMPLE 1

A preparation for perfusion by an intravenous injection was prepared from 0.5 mg of reduced IL2, 5 mg of citric acid, 50 mg of mannitol, 1 ml of sterile water and 50 ml of 5% glucose solution.

EXAMPLE 2

Clinical Study of the Treatment of Pleural Mesothelioma

The study included patients having a histologically confirmed pleural mesothelioma confined to the pleura, possibly extending to the lung, thorax or lymphatic ganglions (stages I, II, III or IV according to Butchart's classification) and having had no previous treatment by chemotherapy or radiotherapy. The patients optionally had undergone treatment by surgical excision and showed a recurrence of the disease.

The IL2 compositions prepared according to the invention allowed the injection of doses of 3 to $24 \times 10^6$ U/M$^2$ per day, according to the patient, by continuous intrapleural perfusion for a cycle of 5 days for the first week, repeated during the third week, then the fifth week of the treatment. The patients who showed a subsequent relapse or only either a partial response or a stabilization of the disease were again treated intrapleurally as described above.

The tumorous lesions of the patients were evaluated before and at the end of the treatment by measuring the macroscopic lesions with a thoracic scanner and by thoracoscopy. An histolgical confirmation was obtained with multiple biopsies of the areas previously affected and random biopsies of the parietal and diaphragm pleurae.

For 11 re-evaluated patients, the following responses were obtained

| PATIENT | Age (years) | Dose of RU 49637 ($10^6$ U/m2/day) | Stage | Response |
|---|---|---|---|---|
| MOU | 64 | 3 | I | CR |
| CAS | 64 | 3 | III | Pg |
| GER | 60 | 6 | II | Pg |
| RAG | 50 | 10 | I | CR |
| CHI | 60 | 10 | III | Pg |
| CHA | 65 | 10 | IV | Pg |
| LLI | 42 | 15 | I$_A$ | CR |
| REY | 59 | 21 | II | Pg |
| SEB | 62 | 21 | I | PR |
| POI | 51 | 21 | II | CR |
| BER | 59 | 24 | II | CR |

The results showed 4 complete responses (CR) and 2 partial responses (PR), that is a response rate of about 50%. A progression (Pg) of the disease was only observed in patients at stage II to IV.

Various modifications of the method of the invention may be made without departing from the spirit or scope thereof and it is to be understood that the invention is intended to be limited only as defined in the appended claims.

What is claimed:

1. A method for treating primary cancers of the pleura in humans comprising administering intrapleurally to humans an amount of a polypeptide having human interleukin 2 activity sufficient to treat primary cancers of the pleura.

2. The method of claim 1 wherein the cancer of the pleura is a mesothelioma.

3. The method of claim 1 wherein the polypeptide is a pure recombinant IL2.

4. The method of claim 3 wherein the polyprotein is a nonglycosylated recombinant IL2 in reduced form.

5. The method of claim 3 wherein the IL2 is administered intrapleurally at a dose of 2 to $25 \times 10^6$ U/M$^2$ per injection.

6. The method of claim 5 wherein the dosage of IL2 is $15 \times 10^6$ U/M$^2$ per day.

7. The method of claim 6 wherein the IL2 is administered in cycles of 5 consecutive days.

8. The method of claim 7 wherein the IL2 is administered in at least two non-consecutive cycles of 5 days.

9. The method of claim 4 wherein the IL2 is administered intrapleurally at a dose of 2 to $25 \times 10^6$ U/M$^2$ per injection.

10. The method of claim 9 wherein the dose of IL2 is $15 \times 10^6$ U/M$^2$ per day.

11. The method of claim 10 wherein the IL2 is administered in cycles of 5 consecutive days.

12. The method of claim 11 wherein the IL2 is administered in at least two non-consecutive cycles of 5 days.

13. A method for treating primary cancers of the pleura in humans having had no previous treatment by chemotherapy or radiotherapy comprising administering intrapleurally to said humans an amount of a polypeptide having interleukin 2 activity sufficient to treat primary cancers of the pleura.

14. The method of claim 13 wherein the polypeptide is a pure recombinant IL 2.

15. The method of claim 14 wherein the polypeptide is a non-glycosylated recombinant IL 2 in reduced form.

* * * * *